United States Patent
Rodriguez-Vilaboa (10) Patent No.: US 8,540,970 B2
(45) Date of Patent: Sep. 24, 2013

(54) COMPOSITION FOR TREATING XEROSTOMIA OR DRY MOUTH

(75) Inventor: Debora Rodriguez-Vilaboa, Madrid (ES)

(73) Assignee: Biocosmetics, S.L., Madrid (ES)

( * ) Notice: Subject to any disclaimer, the term of this patent is extended or adjusted under 35 U.S.C. 154(b) by 852 days.

(21) Appl. No.: 12/036,005

(22) Filed: Feb. 22, 2008

(65) Prior Publication Data

US 2008/0241080 A1    Oct. 2, 2008

Related U.S. Application Data

(60) Provisional application No. 60/891,160, filed on Feb. 22, 2007.

(30) Foreign Application Priority Data

Feb. 22, 2007    (ES) .................................. 200700464

(51) Int. Cl.
*A61K 9/68*    (2006.01)

(52) U.S. Cl.
USPC .......................................................... 424/48

(58) Field of Classification Search
None
See application file for complete search history.

(56) References Cited

U.S. PATENT DOCUMENTS

| | | | |
|---|---|---|---|
| 4,997,654 A | | 3/1991 | Corsello et al. |
| 5,156,845 A | * | 10/1992 | Grodberg ..................... 424/440 |
| 6,156,293 A | | 12/2000 | Jutila et al. |
| 7,074,391 B1 | * | 7/2006 | Alvarez Hernandez ........ 424/49 |
| 7,198,779 B2 | | 4/2007 | Pinol et al. |
| 2005/0281754 A1 | | 12/2005 | Willcox et al. |

FOREIGN PATENT DOCUMENTS

| | | | |
|---|---|---|---|
| AT | 414 095 B | | 9/2006 |
| EP | 1101491 | * | 5/2001 |
| EP | AT414095 | * | 9/2006 |
| ES | 2057412 | | 6/1990 |
| ES | EP 0413427 | * | 6/1990 |
| ES | 2 057 412 | | 10/1994 |
| ES | 2186569 | | 9/2001 |
| ES | EP 1437126 | * | 9/2002 |
| ES | 2 186 569 | | 5/2003 |
| WO | WO9829090 | * | 7/1998 |

OTHER PUBLICATIONS

Buchalla, et al., "Influence of Olive Oil Emulsions on Dentin Demineralization in vitro", Caries Research, 2003, pp. 100-107, vol. 37, S. Karger AG, Basel.

Featherstone, et al., "Lipid Effect on the Progress of Artificial Carious Lesions in Dental Enamel", Caries Research, 1984, pp. 52-55, vol. 18.

Jenkins, et al., "The Effect of Daily Gum-chewing on Salivary Flow Rates in Man", J. Dent. Res., May 1989, pp. 786-790, vol. 68, No. 5.

(Continued)

*Primary Examiner* — Brian Gulledge
*Assistant Examiner* — Snigdha Maewall
(74) *Attorney, Agent, or Firm* — Sughrue Mion, PLLC (57) ABSTRACT

The present invention provides a composition comprising olive oil, trimethylglycine and xylitol for treating xerostomia and disorders associated thereto, with very good results in increasing the unstimulated salivary flow, in alleviating the symptoms of xerostomia, including the pain associated to xerostomia, as well as improving the quality of life of affected persons. The composition of the invention has also been proved to protect dentin against demineralization in acid conditions.

12 Claims, 4 Drawing Sheets

(56) References Cited

OTHER PUBLICATIONS

Aguirre-Zero, et al., "Effect of Chewing Xylitol Chewing Gum on Salivary Flow Rate and the Acidogenic Potential of Dental Plaque", Caries Research, 1993, pp. 55-59, vol. 27, S. Karger AG, Basel.

Giertsen, et al., "Effects of Mouth Rinses with Xylitol and Fluoride on Dental Plaque and Saliva", Caries Research, 1999, pp. 23-31, vol. 33, S. Karger AG, Basel.

Haveman, et al., "Dental Management and Treatment of Xerostomic Patients", Texas Dental Journal, Jun. 1998, pp. 43-56.

Kelly, et al., "Bioadhesive, rheological, lubricant and other aspects of an oral gel formulation intended for the treatment of xerostomia," International Journal of Pharmaceutics, 2004, pp. 391-406, vol. 278, Elsevier B.V.

Meyer-Lueckel, et al., "The effect of commercially available saliva substitutes on predemineralized bovine dentin in vitro", Oral Diseases, 2002, pp. 192-198, vol. 8, Blackwell Munksgaard.

Eva Soderling et al., "Betaine-containing toothpaste relieves subjective symptoms of dry mouth", Institute of Dentistry, University of Turku, Turku, Finland, Acta Odontol Scand 1998;56, pp. 65-69.

Ship, J.A. et al, "Safety and effectiveness of topical dry mouth products containing olive oil, betaine, and xylitol in reducing xerostomia for polypharmacy-induced dry mouth", Journal of oral rehabilitation, 2007, vol. 34, pp. 724-732, p. 726, col. 1.

* cited by examiner

COMPOSITION FOR TREATING XEROSTOMIA OR DRY MOUTH

FIELD OF THE INVENTION

The invention refers to the field of treatment of oral cavity disorders. Specifically, the invention refers to a composition for treating xerostomia and its associated problems.

BACKGROUND OF THE INVENTION

Saliva is a natural fluid whose function is essential for oropharyngeal, digestive and general health. Salivary function is apparently simple; however, the complexity of its composition reflects its large number of properties. When the amount or quality of saliva diminishes, multiple problems occur called xerostomia or "dry mouth" or "burning mouth".

The WDF (World Dental Federation) defines it as the "modern man's disease" due to its high incidence. The percentages it has established range from 20% in people around 20 years of age, and 40% in people of 60 years of age, being higher in older age groups.

Xerostomia or dry mouth is a universal problem that can affect anybody, independently of their sex, race, age or other conditions. However, it is more frequent in women than in men, mainly due to the reduction of oestrogen hormones in perimenopause, in the same manner as dryness appears in other mucosa such as the vagina and the eyes. One of every four adults suffers from dry mouth. Furthermore, it is associated to multiple systemic and psychiatric diseases, and more importantly, it appears as a secondary effect to multiple treatments of these and other diseases that are becoming more frequent, even reaching epidemic characteristics. Among these are diabetes, cancer, anxiety, depression, allergies, autoimmune diseases, stress or alcoholism, for example.

It is for all the former that xerostomia or "dry mouth syndrome" is so relevant today. Furthermore, it is a syndrome that can be silent in many cases and that may not show symptoms until it is very advanced. 50% of xerostomia patients do not show any symptoms, and what is scientifically more relevant, up to 50% of salivary flow may be lost without yet perceiving dryness in the mouth or before xerostomia manifests itself with signs or symptoms.

Xerostomia or dry mouth syndrome affects both people with dentition (toothed patients) and toothless patients. The consequences of said xerostomia in the first group are very manifest, since an alteration of the natural buffering capacity of saliva also occurs a few months after syndrome instauration, due to the deficit in salivary flow, leading to short-term structural deterioration of the hard tissues in the mouth (teeth).

In toothed patients with xerostomia, the saliva that under normal physiological conditions acts as a defence, barrier and reinforcement, is no longer effective or sufficient to slow down the demineralization of enamel and dentin caused by daily aggressions (cariogenic bacteria, acids, drops in pH, dental bruxism or clenching . . . ) Thus, for example, rapidly evolving caries and atypical caries such as neck caries occur as a result of the postprandial (after eating) decrease in oral pH, which can completely destroy teeth in a few months. Furthermore, a whole series of symptoms and signs can occur, independently of whether there are teeth or not, which can even alter the patient's quality of life.

In toothless patients, xerostomia does not cause dental destruction since the patient has already lost all his teeth. However, the appearance of signs and symptoms can be even greater than for the first group.

Different types of glands are responsible for said secretions: mucilaginous saliva is secreted by the minor salivary glands (labial, palatine, lingual), whereas aqueous saliva is secreted by the parotid and submaxillary glands in much larger amounts.

Dry mouth symptoms are frequently present in patients whose salivary secretion, both stimulated and unstimulated, is normal. In contrast, there are patients with true hyposalivation who do not complain of buccal dryness. Perception by the patient largely depends on the salivary component that is lacking: buccal dryness is felt when mucilaginous components are missing (scientifically called resting or unstimulated saliva) which lubricate and provide comfort, although the amount of salivary flow (flow of aqueous or stimulated saliva) may be the same. In contrast, patients with a decrease in salivary flow may not perceive dryness if they preserve mucilaginous saliva.

Today it is known that it is resting or unstimulated saliva which prevents the symptoms and protects both soft tissues (tongue and mucosa) and hard tissues (teeth). A comparison could be made with tears (crying) when upset, which do not perform the function of protecting the eye, since they fall down the face, very different to lachrymal secretion that lubricates and protects ocular structures from the external medium, protecting normal vision.

Both kinds of saliva, stimulated and unstimulated or resting, are notably different in volume, glandular origin and composition. Resting saliva is that which lubricates and provides the feeling of calmness. One of the preferred theories indicates that this may be due to the high concentration of potassium ions in their buffer system, which, scientifically, is the most used cation in desensitizing toothpastes and gels. In contrast, stimulated saliva has large amounts of sodium.

There is great individual variability regarding salivary flow. It can differ by up to 50%.

Xerostomia makes talking, chewing and swallowing difficult, and also oral hygiene since it favours the accumulation of dental plaque because the salivary flow no longer washes out bacteria. Furthermore, it reduces the buffer effect of saliva, making the pH become acid and destroying the teeth. It is related to many chronic pharyngitis, mucositis and even to digestive disorders. At a local level it can cause a feeling of burning and/or pain in the soft tissues and in the tongue, a need for moisturizing the mouth at short time intervals, leaves surfaces of the teeth rough, a sliver of saliva between the teeth or the tongue and the palate, a feeling of pressure or tightness in a group of teeth and even pain. It causes a fast progression of tooth decay, it facilitates periodontal diseases (gingivitis), and it wears out teeth due to greater abrasion and friction without lubrication between dental surfaces. It also causes fissures in the lips and bacterial infections (candidiasis, sialodentitis), halitosis, and it can even produce eating disorders, insomnia, irritability or depression. Likewise, xerostomia affects the sufferer's quality of life from the point of view of sociability: there is a lack of interest for eating in company, for going out or for talking in groups.

The ethiology of xerostomia involves many factors and is highly complex:

1. Consumption of mouth-drying drugs: More than 500 families of drugs have xerostomia as a side effect, this being one of the main reasons for medication discontinuation by patients. These are responsible for most cases of xerostomia. Salivary deficiency usually lasts a long time after an extended treatment, despite drug discontinuation.

The drugs that produce this effect most frequently are diuretics (hydrochlorothiazide, amiloride), sedatives, antidepressants (serotonin reuptake inhibitors and especially tricyclic antidepressants), antihypertensives, antiinflammatory drugs, decongestants (phenylpropanolamine, pseudoephedrine), anxiolytic drugs (diazepam), anticholinergic-type antispasm drugs (atropine, oxybutynin), antidiarrheal (loperamide, diphenoxylate), antihistamines (chlorphenamine, loratadine), non-steroid antiinflammatory drugs (piroxicam, ibuprofen), opioid analgesics (morphine), muscle relaxants (baclofen), bronchodilators (ipratropium, salbutamol), antiparkinson drugs (levodopa, biperiden), antiacne drugs (isotretinoin) and antipsychotics such as phenothiazines and butyrophenones.

2. Oncological treatments such as head and neck radiotherapy (one of the most widely recognised causes). Also, and more frequently, oncological chemotherapy. And also radioactive iodine therapy in thyroid carcinoma.

3. Autoimmune diseases: they permanently reduce salivary flow. We can highlight Sjögren's Syndrome, systemic lupus erythematosus, rheumatoid arthritis, polymyositis/dermatomyositis and scleroderma.

4. Infectious diseases: HIV, hepatitis.

5. Transplant patients with immunosuppressive therapy: salivary gland hypofunction.

6. Dialysis patients.

7. Systemic diseases such as diabetes, arthritis, Alzheimer and senile dementia.

8. Psychiatric diseases such as anxiety, depression and nervous anorexia.

9. Consumption of addictive substances such as alcohol, tobacco and drugs. A common factor in our times.

In any case, it is important to diagnose and treat xerostomia because as well as the loss of quality of life for the patient, it also seriously affects the patient's health.

This shows that xerostomia is a very complex syndrome. Until now there have only been failed attempts regarding treatment, focused on imitating natural saliva with artificial products that try to substitute the absent natural saliva.

Thus, until now attempts had been made in the sense of creating artificial salivas, although said products are not exempt of critiques, since in general, due to their rheologic and organoleptic features, they are usually gels with acid, even very acid, pH levels, with the subsequent risk this entails for the dry mouth patient. ("Dental Management and Treatment of Xerostomic Patients", by Dr. Carl W. Haveman, D.D.S., M.S., Director, Advanced General Dentistry Clinic, The University of Texas Health Science Center at San Antonio—*Texas Dental Journal*, June 1998, pp. 43 to 56); "The effect of commercially available saliva substitutes on pre-demineralised bovine dentin in vitro", by Department of Operative Dentistry and Periodontology. University School of Dental Medicine, Freie Unversitaet, Berlin, Germany—*Oral Diseases* #8, pp. 192-198).

Therefore, there is still a need in the state of the art for providing alternative compositions for treating xerostomia that increase the flow of resting or unstimulated saliva.

The present inventors have discovered that the combination of olive oil, trimethylglycine and xylitol has a synergic effect since it surprisingly achieves increasing in almost 200% the salivary flow of resting or unstimulated saliva, managing to alleviate the symptoms of dry mouth syndrome, including pain, and improving the quality of life of patients.

A study by Kelly et al. ("Bioadhesive, Theological, lubricant and other aspects of an oral gel formulation intended for the treatment of Xerostomia", H. M. Kelly, P. B. Deasy, M. Busquet, A. A. Torrance. School of Pharmacy, Trinity College, University of Dublin, Ireland—*International Journal of Pharmaceutics* 2004 #278, pp. 391-406), describes an artificial saliva with sialogogues or stimulants based on potassium chloride, sodium chloride, calcium chloride and magnesium chloride, which are also those which increase the flow of stimulated saliva and which can also comprise sunflower oil or olive oil in order to improve the bioadhesion and viscosity thereof, although the authors indicate the curiosity that the saliva is neither sticky or viscous. The use of olive oil has also been described as a greasy vehicle in compositions for treating dermatological disorders related to dry mucosa (patents US 200528174 and AT 414095).

Xylitol has been included as an ingredient in numerous products for dry mouth, with a proven benefit as a non-carcinogenic sweetening agent (see, for example, patent ES 2186569). However, it has not been possible to prove its capacity per se for stimulating salivary flow (Caries Res. 1993; 27(1):55-9; Caries Res. 1999; 33(1):23-31). In fact, its function as a salivary stimulant in chewing gum and confectionery products, described in patent ES 2057412, for example, seems to be due more to the vehicle, since any gum, hard or soft plastic in the mouth is capable of promoting stimulated salivary flow even without any active ingredients (J. Dent. Res. 1989; 68(5):786-90).

On the other hand, U.S. Pat. No. 5,156,845 describes the use of betaine hydrochloride to stimulate stimulated salivary flow based on the acidity the molecule contributes to the composition. Likewise, U.S. Pat. No. 6,156,293 by Jutila, defines the use of trimethylglycine to alleviate the symptoms of dry mucosa and membranes of the body in non-therapeutic preparations, since they do not increase any vital physiological function. The author describes trimethylglycine as a bipolar compound that can adhere to the surface of mucosal membranes and stay there for some time binding water and thus moistening them.

However, the combined use of olive oil, xylitol and trimethylglycine has not been described in the state of the art as a therapeutic composition for improving salivary physiological function in treating xerostomia. The composition of the invention does not only achieve alleviating the most important symptoms of this serious problem, but also, thanks to the surprising increase in unstimulated salivary flow, it achieves all the benefits provided by natural saliva.

Furthermore, also surprisingly, said synergic combination is capable of protecting against dentin demineralization, whereas none of the ingredients separately achieves this, thus preventing or reducing problems related to xerostomia such as caries, for example.

Buchalla et al. ("Influence of Olive Oil Emulsions on Dentin Demineralization in vitro", W. Buchalla, T. Attin, P. Roth, E. Hellwig. Freiburg University, Germany—*Caries Research* 2003 #37, pp. 100 to 107), have described the protective effect against dentin demineralisation of oily emulsions with 5% and 50% of olive oil, concluding that the latter protects more than the first, but without significant differences. Likewise, the studies by Featherstone and Rosenberg (*Caries Res* 18 (1984) 52-55) had shown that lipids provide a diffusion film in the organic aquo-lipo-proteic matrix of enamel, hindering the occurrence of caries.

On the other hand, the results obtained from the erosion protection studies enclosed do not reveal any capacities of olive oil for protecting against demineralisation under the conditions in which the combination of the three ingredients do so in enamel and dentin.

Furthermore, the combination of the three components of the composition of the invention has not been suggested or described to have such a surprising effect regarding preventing the loss of dentin, greater than that provided by the ingredients independently. This property is especially important in xerostomia patients, since gum dehydration produces an exposure of dentin, which is especially sensitive to demineralisation.

Therefore, the composition of the present invention combining the active ingredients mentioned allows treatment of xerostomia or disorders associated with it with very good results in increasing the flow of resting saliva, in alleviating the symptoms and pain associated to xerostomia as well as improving the quality of life of affected persons. Furthermore, the composition of the invention has been proved to protect against demineralisation of dentin subjected to extreme pH conditions similar to those existing in the mouth without saliva.

OBJECT OF THE INVENTION

The object of the present invention, therefore, is to provide a composition for treating xerostomia, comprising a synergic combination of olive oil, trimethylglycine and xylitol.

DETAILED DESCRIPTION OF THE INVENTION

The present invention provides a composition for treating xerostomia comprising olive oil, trimethylglycine and xylitol, hereinafter "composition of the invention".

Within the context of the invention, the term "composition for treating xerostomia" refers to a composition that improves the physiological function, that is, increases the flow of unstimulated saliva in a physiological manner. Hence, it is a therapeutic composition and not a mere oral hygiene product. Furthermore, said composition alleviates the symptoms thereof, including xerostomia-associated pain, and improves the quality of life of the persons affected. The composition has also proved to be effective in preventing the demineralisation caused by acids.

As has been previously indicated, the invention is aimed at preserving and increasing natural salivary flow for "resting saliva" by the use of a novel and innovative topical therapeutic composition. It has the advantage that it can be applied "ad libitum", that is, when needed (the patient suffers from dry mouth all day long, even at night), without the side effects of stimulating drugs known until now, such as in the case of pilocarpine.

The composition of the invention, by stimulating salivary flow, manages to increase the amount of calcium, potassium, phosphate and bicarbonate ions, as well as of the rest of beneficial components that natural human saliva contains, such as proteins, immunoglobulins, peroxidase, etc.

In a particular embodiment, the composition of the invention comprises 0.1-4% by weight of olive oil. In a preferred embodiment, the composition of the invention comprises 0.2-3% by weight of olive oil. In an even more preferred embodiment, the composition of the invention comprises 2% by weight of olive oil.

In a particular embodiment, the composition of the invention comprises 0.1-6% by weight of trimethylglycine. In a preferred embodiment, the composition of the invention comprises 4% by weight of trimethylglycine.

In a particular embodiment, the composition of the invention comprises 1-50% by weight of xylitol. In a preferred embodiment, the composition of the invention comprises 5-30% by weight of xylitol. In an even more preferred embodiment, the composition of the invention comprises 10% by weight of xylitol.

In a preferred embodiment, the composition of the invention comprises 2% by weight of olive oil, 4% by weight of trimethylglycine and 10% by weight of xylitol. In another preferred embodiment, the composition of the invention comprises 2% by weight of olive oil, 2% by weight of trimethylglycine and 1% by weight of xylitol.

In another particular embodiment, the composition of the invention can further comprise one or more components such as remineralising agents, viscosity-controlling agents, moisturising agents, preservatives, colorants, buffer agents, sweeteners, proteolytic enzymes, emulsifiers, abrasives, essential oils, cicatrizing agents, aromas, antioxidants, animal or plant gelatines, excipients, and a mixture thereof.

Among these supplementary ingredients we can highlight the agents that improve remineralising capacity, since they contribute ions that allow remineralisation, specifically fluorine from any appropriate source, calcium from any appropriate source, as well as phosphates or other ions with remineralising capacity and capable of hardening the teeth.

Therefore, in a preferred embodiment, the composition of the invention comprises a remineralising agent chosen among fluoride anions, phosphate anions, sodium cations and potassium cations.

Among the aforementioned we can cite the following as examples: potassium fluoride, sodium fluoride, sodium monofluorophosphate, tin fluoride, amine fluorides (hexadecylamine hydrofluoride, bis-(hydroxyethyl)aminopropyl-N-hydroxyethyl-octadecylamine dihydrofluoride, N—N',N'-tri(polyoxyethylene)-N-hexadecyl-propylenediamine dihydrofluoride or octadecenylamine hydrofluoride), potassium phosphate, potassium pyrophosphate, tripotassium citrate, calcium lactate, calcium pantothenate and calcium carbonate.

Likewise, any rheologic agent known in the state of the art can be used as viscosity-controlling agents, such as gum arabic, tragacanth gum, xanthan gum, carboxymethyl cellulose (CMC), carbopol-type polymers, pectins or mucines.

Likewise, any moisturising agent of the state of the art can be used in the composition of the invention, such as, for example, glycerine, propylene glycol or sorbitol.

Among the preservatives that can be used in the composition of the invention we can mention sodium benzoate, benzoic acid, diazolinyl urea, imidazolinyl urea, sodium methylparaben, sodium propylparaben, among other preservatives of the state of the art.

On the other hand, any colorant of the state of the art can be used in the composition of the invention, such as, for example, C.I. 75810 or titanium dioxide.

Likewise, in the composition of the invention any buffer agents or pH-regulating agents known in the state of the art can be used, among which we can mention the following: lactic acid and lactates, citric acid and citrates, malic acid and salts thereof, sodium hydroxide, potassium phosphate and potassium pyrophosphate.

Among the sweeteners that can be used in the composition of the invention we can mention maltitol, isomaltitol, manitol, lactitol, sodium saccharine, acesulfame potassium, aspartame, cyclamate, taumatin or neohesperidine DC, among other known sweeteners.

Proteolytic enzymes such as papain, for example, can also be incorporated to the composition of the invention.

Likewise, any suitable emulsifier of the art can be used in the composition of the invention, such as, for example, PEG-40 hydrogenated castor oil or lecithin.

On the other hand, any abrasive used in this field of the art can be used in the composition of the invention, such as hydrated silicas (Syloid 244, Zeodent 163 or Zeodent 623, for example).

Likewise, the composition of the invention can incorporate essential oils such as parsley seed oil or citrus medica extract, to name a few.

Another optional component of the composition of the invention is any cicatrizing agent of the art such as allantoin, D-panthenol, calcium pantothenate, for example.

Likewise, the composition of the invention can comprise a suitable antioxidant of the state of the art such as tocopherol acetate or vitamin C.

On the other hand, the composition of the invention can comprise animal or plant gelatines such as bovine gelatine, fish gelatine or algae gelatine, for example.

The composition of the invention can also include aromas such as citrus medica or mint extracts, for example.

Finally, suitable excipients will be added to the composition of the invention according to the formulation they are intended for. Thus, beeswax, gum base, carnauba wax or shellac, etc can be used.

In the case of liquid and doughy preparations, water is used as a solvent.

The composition of the invention, which comprises olive oil, trimethylglycine and xylitol, has a neutral pH in order to guarantee indemnity of the enamel and dentin of dry mouth patients. Furthermore, the invention does not contemplate the use of sodium lauryl sulphate, sodium lauryl sarcosinate, cocamidopropyl betaine (do not mistake with betaine) and detergents commonly used in oral hygiene products and which are associated to the occurrence of recurrent sores and ulcerations (Herlofson B). Likewise, it lacks alcohol in order to prevent association between the latter and oral cancer, and essentially, to prevent its known dehydrating effect.

As has been indicated, according to the desired presentation it can include at each time all that necessary for it to have the necessary organoleptic and rheologic form.

In a particular embodiment, the composition of the invention is formulated as a toothpaste, mouthwash, salivary substitute, spray, gel, chewing gum, suckable capsules, suckable lozenges, palate sheets, tablets, sweets, impregnated oral swabs, impregnated oral gauzes, suckable single-dose presentations of frozen solution.

In general, as well as the swabs and gauzes, any suitable support impregnated with a solution of the invention can be used for topical application in the mouth. Likewise, a single-dose presentation (a suitable sachet or blister, for example) of the solution of the invention that is frozen before use can be used. Thus, to the effect of the novel composition of the invention is added the effect of the cold in order to achieve faster and more effective alleviation from the pain associated to xerostomia.

In any case, the expert in the art will formulate the composition of the invention in any suitable presentation that allows a simple use thereof for the xerostomia patient in order to calm pain and stimulate salivary flow.

The composition of the invention has been proved to triplicate salivary flow for resting saliva, increasing it by almost 200%. Said combination has also been proved to improve the symptoms, the pain and quality of life associated to dry mouth syndrome.

Furthermore, and surprisingly, said association is capable of protecting against dentin demineralisation.

The composition comprises ingredients the novel combination of which has been proved to have very beneficial effects for dry mouth but which, however, do not individually present the effectiveness proved for the composition.

The following examples illustrate the invention and should not be considered as limiting the scope thereof.

Example 1

Toothpaste Formulation

| Component | Percentage (w/w) |
|---|---|
| Olive oil | 2.000 |
| Trimethylglycine | 4.000 |
| Xylitol | 10.000 |
| Glycerine | 31.400 |
| Water | 27.950 |
| Zeodent 163 | 10.000 |
| Zeodent 623 | 6.000 |
| Tetrapotassium pyrophosphate | 2.300 |
| Syloid 244 | 2.000 |
| D-Panthenol | 0.050 |
| Tocopherol acetate | 0.050 |
| Titanium dioxide | 1.000 |
| Papain | 0.100 |
| Potassium phosphate | 0.900 |
| Citrus medica | 0.500 |
| Xanthan gum | 1.000 |
| Sodium fluoride | 0.220 |
| Sodium saccharine | 0.130 |
| Diazolinyl urea | 0.100 |
| Parsley oil | 0.300 |
| TOTAL | 100 |

Example 2

Mouthwash Formulation

| Component | Percentage (w/w) |
|---|---|
| Olive oil | 0.200 |
| Trimethylglycine | 2.000 |
| Xylitol | 1.000 |
| Water | 90.095 |
| PEG-40 hydrogenated castor oil | 2.000 |

-continued

| Component | Percentage (w/w) |
| --- | --- |
| Glycerine | 2.000 |
| Propylene glycol | 1.000 |
| Citrus medica | 0.400 |
| Diazolinyl urea | 0.300 |
| Lactic acid | 0.200 |
| Allantoin | 0.200 |
| Sodium methylparaben | 0.200 |
| Sodium propylparaben | 0.150 |
| Potassium fluoride | 0.070 |
| C.I. 75810 | 0.050 |
| D-Panthenol | 0.050 |
| Tocopherol acetate | 0.050 |
| Aroma | 0.005 |
| Parsley oil | 0.030 |
| TOTAL | 100 |

Example 3

Mouthwash Formulation

| Component | Percentage (w/w) |
| --- | --- |
| Olive oil | 2.000 |
| Trimethylglycine | 2.000 |
| Xylitol | 1.000 |
| Water | 81.859 |
| PEG-40 hydrogenated castor oil | 10.300 |
| Citrus medica | 0.400 |
| Sodium methylparaben | 0.200 |
| Sodium propylparaben | 0.100 |
| Sodium benzoate | 0.130 |
| Benzoic acid | 0.200 |
| Allantoin | 0.200 |
| Potassium fluoride | 0.070 |
| C.I. 75810 | 0.050 |
| D-Panthenol | 0.500 |
| Tocopherol acetate | 0.500 |
| Aroma | 0.205 |
| Parsley oil | 0.286 |
| TOTAL | 100 |

Example 4

Salivary Substitute Formulation

| Component | Percentage (w/w) |
| --- | --- |
| Olive oil | 1.000 |
| Trimethylglycine | 4.000 |
| Xylitol | 10.000 |
| Glycerine | 42.602 |
| Water | 30.000 |
| Tripotassium citrate | 6.050 |
| Carbopol 980 | 1.500 |
| Potassium pyrophosphate | 1.150 |
| Xanthan gum | 1.000 |
| Calcium lactate | 1.000 |
| Citrus medica | 0.500 |
| Potassium phosphate | 0.450 |
| Sodium benzoate | 0.400 |
| Sodium saccharine | 0.100 |
| Tocopherol acetate | 0.050 |
| D-Panthenol | 0.050 |
| Parsley oil | 0.148 |
| TOTAL | 100 |

Example 5

Spray Formulation

| Component | Percentage (w/w) |
| --- | --- |
| Olive oil | 1.000 |
| Trimethylglycine | 2.000 |
| Xylitol | 10.000 |
| Water | 75.002 |
| PEG-40 hydrogenated castor oil | 5.750 |
| Glycerine | 2.000 |
| Propylene glycol | 1.000 |
| D-Panthenol | 0.500 |
| Tocopherol acetate | 0.500 |
| Calcium lactate | 0.500 |
| Diazolinyl urea | 0.450 |
| Citrus medica | 0.400 |
| Allantoin | 0.200 |
| Sodium methylparaben | 0.200 |
| Lactic acid | 0.200 |
| Sodium propylparaben | 0.150 |
| Parsley oil | 0.143 |
| Aroma | 0.005 |
| TOTAL | 100 |

Example 6

Efficacy of the Composition of the Invention in a Population of Adults Suffering Symptoms of Hyposalivation and Xerostomia.

Materials and Methods

Subjects

A total of 40 participants were recruited and enrolled from a general population aged 50-67 years.

All the subjects reported a history of dry mouth symptoms due to polypharmacy. All the subjects complied with the following requirements:

| | |
| --- | --- |
| No. 1 | Subjects suffering from dry mouth symptoms valued above 30 mm on at least one of the eight questions of the dry mouth VAS questionnaire. |
| No. 2 | Subjects with an unstimulated salivary flow equal to or below 0.2 ml/minute. |
| No. 3 | Subjects between 50 and 90 years of age. |
| No. 4 | Subjects taking at least three drugs associated with the hypofunction of salivary glands or xerostomia (anxiolytics, anorexiants, anti-asthmatics, anti-cholinergics, anti-depressants, anti-emetics, anti-histamines, anti-hypertensives, anti-parkinsonians, anti-psychotics, decongestants, diuretics or sedatives, for example) |
| No. 5 | Subjects taking drugs according to the previous point for at least one week before the start of the study. |
| No. 6 | Subjects willing to use only the products indicated by the coordinator during each phase of the study. |
| No. 7 | Subjects willing to assist to all visits required for the study. |

The subjects were randomly separated into two groups. Each group, made up of 20 individuals, used both products (control product and tested product) in order to ensure that the results are not subject to the idiosyncrasy of the patients (crossover study).

Unstimulated whole saliva was collected according to a previously described protocol (Navazesh M. "Methods for collecting saliva", Annals of the New York Academy of Sciences, 1993; 694:72-7) at the same time as a standardized oral tissue examination was performed. The coordinator responsible for the study facilitated a xerostomia VAS questionnaire with eight assessments of 100 mm each together with a questionnaire aimed at evaluating quality of life associated with xerostomia.

Products of the Study

Topical dry mouth products were used containing the three active ingredients (olive oil, trimethylglycine and xylitol) formulated at neutral pH.

Specifically, the tested products were formulated in four different presentations: Toothpaste, mouthwash, spray and gel.

The standard regime for the products tested consisted in: (1) Using the toothpaste/mouthwash three times a day after main meals, and (2) using the spray and gel between meals a minimum of eight times a day.

As a reference or control the subjects were asked to follow their usual treatment regime for dry mouth.

Study Design

All patients were subjected to a series of baseline measurements consisting in the measurement of unstimulated salivary flow according to a previously described protocol (Navazesh, supra) at the same time as a standardized oral tissue examination was performed.

The coordinator responsible for the study facilitated a xerostomia VAS questionnaire with eight assessments of 100 mm each together with a questionnaire aimed at evaluating quality of life related to xerostomia.

The subjects were randomly separated and assigned to protocol 1 or protocol 2.

Protocol 1. The patients carried on with their usual regime for dry mouth treatment, excluding the use of any pharmacological salivary stimulant. On the eighth day, all subjects returned to the research centre, where the baseline measurements were repeated and possible adverse effects were recorded.

Then a crossing was performed so that patients then used the products to be tested. Fifteen days after the beginning of the study, all subjects returned to the research centre. The baseline tests were repeated and possible side effects were recorded. The subjects of this group then finished the study.

Protocol 2. The patients used the products tested according to the standard usage regime. On the eighth day, all subjects returned to the research centre, where the baseline measurements were repeated and possible side effects were recorded.

Then a crossing was performed so that the patients went on to a washout period during which they could not use any kind of products for dry mouth treatment.

Fifteen days after the beginning of the study, the subjects returned to the research centre. The baseline tests were repeated and possible adverse effects were recorded. They then went on to use their usual dry mouth treatment regime once again. 22 days after the beginning of the study, this group returned to the research centre. The baseline tests were repeated and possible side effects were recorded. After this, the study was finished.

Unstimulated Salivary Flow Measurements

Unstimulated whole saliva was collected according to a previously described protocol (Navazesh, supra) at the same time as a standardized oral tissue examination was performed.

Xerostomia VAS Questionnaire

A validated xerostomia VAS (Visual Analogue Scale) questionnaire was used, which focuses on eight aspects of dry mouth (Pai S, et al. "Development of a Visual Analogue Scale questionnaire for subjective assessment of salivary dysfunction", Oral Surgery, Oral Medicine, Oral Pathology, Oral Radiology, & Endodontics, 2001; 91(3):311-6). The subjects were asked to make a mark on a 100 mm horizontal line to indicate the level of dryness they suffered. Two of the aspects covered (No. 2 and 3) in the questionnaire are related with salivary gland hypofunction (Fox et al. "Subjective reports of xerostomia and objective measures of salivary gland performance", Journal of the American Dental Association, 1987; 115(4):581-4). Three of the aspects (No. 6, 7 and 8) have been previously used in dry mouth research (Fox et al., supra; Närhi T O. "Prevalence of subjective feelings of dry mouth in the elderly", Journal of Dental Research, 1994; 73(1):20-5), and dryness of lips (No. 6) successfully predicted salivary gland hypofunction (Navazesh M, et al., "Clinical criteria for the diagnosis of salivary gland hypofunction", Journal of Dental Research, 1992; 71(7):1363-9). The aspects mentioned are:

| | |
|---|---|
| No. 1 | Evaluates the difficulty experienced when speaking due to dryness |
| No. 2 | Evaluates the difficulty experienced when swallowing due to dryness |
| No. 3 | Evaluates how much saliva you have in your mouth |
| No. 4 | Evaluates dryness of your mouth |
| No. 5 | Evaluates dryness of your throat |
| No. 6 | Evaluates dryness of your lips |
| No. 7 | Evaluates dryness of your tongue |
| No. 8 | Evaluates your thirst level |

Questionnaire on Quality of Life Related to Xerostomia

The questionnaire on quality of life related to xerostomia used in the study includes 12 questions extracted from a validated form (Henson B S et al., "Preserved salivary output and xerostomia-related quality of life in head and neck cancer patients receiving parotid-sparing radiotherapy", Oral Oncology, 2001; 37(1):84-93). This questionnaire is aimed at analysing how dry mouth affects a person's quality of life. The questions are classified in three groups: physical function, personal function and pain. The questions covered were:

| | |
|---|---|
| PHYSICAL FUNCTION | |
| No. 1 | The dryness of my mouth/throat limits the type of food or the amount of food in my diet |
| No. 2 | The dryness of my mouth/throat makes me feel uncomfortable when I speak in front of somebody |
| No. 3 | The dryness of my mouth/throat interferes with my daily activity |
| No. 4 | The dryness of my mouth/throat makes the food I eat not taste good |
| PAIN | |
| No. 5 | The dryness of my mouth/throat is uncomfortable |
| No. 6 | The dryness of my mouth/throat keeps me worried and conscious of the problem |
| No. 7 | The dryness of my mouth/throat makes me feel nervous |
| No. 8 | The dryness of my mouth/throat prevents me from enjoying life |
| PERSONAL FUNCTION | |
| No. 9 | The dryness of my mouth/throat makes me worry about the appearance of my mouth and teeth |
| No. 10 | The dryness of my mouth/throat reduces my happiness |
| No. 11 | The dryness of my mouth/throat affects all the aspects of my life |
| No. 12 | If you had to spend the rest of your life with the dryness of the mouth/throat that you experience now, how would you feel? |

The possible answers to the first 11 questions were: (1) not at all, (2) very little, (3) a little, (4) quite a bit and (5) a lot. For question 12, the possible answers were: (1) delighted, (2) satisfied, (3) neither satisfied nor unsatisfied, (4) clearly unsatisfied, and (5) terrible.

Results

Forty (40) subjects were selected to form part of the study, 39 of which completed all the visits.

The analysis of variance indicated that there were no significant differences between the initial unstimulated salivary flow between the patients forming part of protocol 1 (0.046 ml/min) and the patients forming part of protocol 2 (0.047 ml/min). This ensures that the differences found at the end of the study are due to the different treatments and not to initial differences between the groups.

Unstimulated Salivary Flow Measurements

Figure 1:
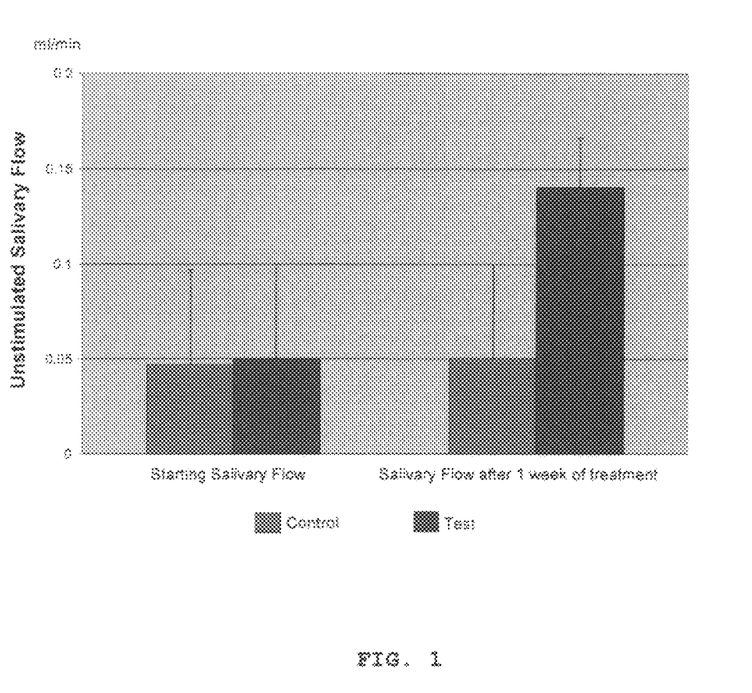
FIG. 1 represents the values of unstimulated salivary flow at the beginning and after one week of topical application of usual products for dry mouth (control) and of the composition of the invention (test).

FIG. 1 represents the values of unstimulated salivary flow at the beginning and after one week of topical application of usual products for dry mouth (control) and of the composition of the invention (test). The difference between the groups, approximately 180%, is statistically significant at p=0.033.

The results show that the use of the products tested comprising olive oil, trimethylglycine and xylitol for one week resulted in an increase in unstimulated salivary flow with respect to the group that used its normal treatment routine for dry mouth (p=0.033). The average salivary flow in the group that used the tested product (olive oil, trimethylglycine and xylitol) passed from 0.05 ml/min±0.05 ml/min (mean±standard deviation) to 0.140 ml/min±0.26 ml/min (mean±standard deviation), whereas the salivary flows in the subjects that followed their daily routine kept constant after a period of 7 days (0.047 ml/min±0.05 versus 0.05 ml/min±ml/min; mean±standard deviation).

Xerostomia VAS Questionnaire

Figure 2:
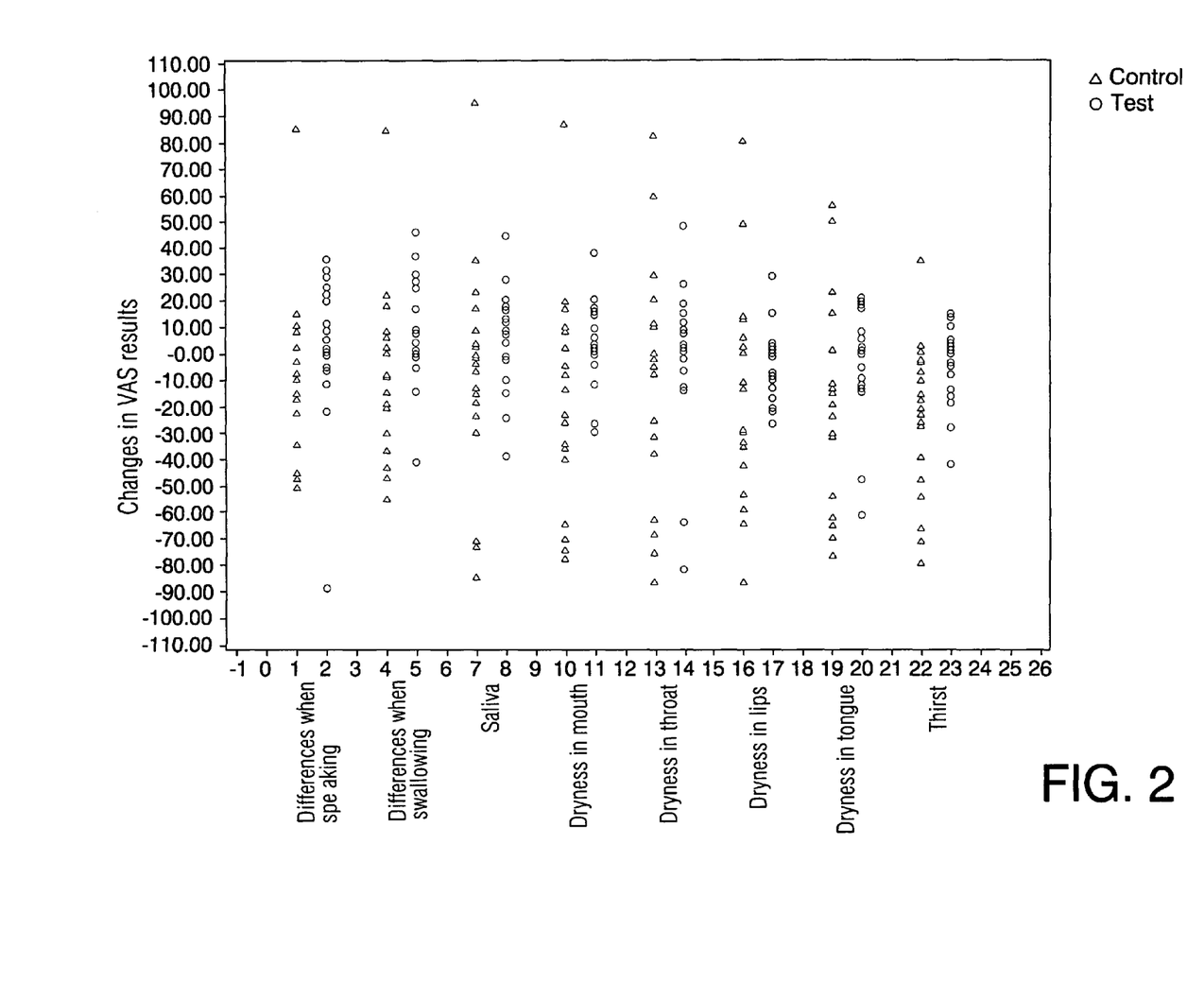
FIG. 2 represents the change of symptoms according to the results of the Xerostomia VAS questionnaire after one week of topical application of usual products for dry mouth (control) and of the composition of the invention (test).

FIG. 2 shows the change of symptoms according to the results of the xerostomia VAS questionnaire after one week of topical application of usual products for dry mouth (control) and of the composition of the invention (test). Positive changes imply a reduction of symptoms, negative changes imply an increase of symptoms, and neutral changes imply that there are no changes. The difference between the groups for the group of the eight questions is statistically significant (p=0.011).

The results of the xerostomia VAS questionnaire demonstrated that the use of the tested products also produced an improvement of symptoms generally greater than that produced by the products of their usual regimes for treating dry mouth (control) (p=0.011) for the same time period.

Questionnaire on Quality of Life Related to Xerostomia

Figure 3:
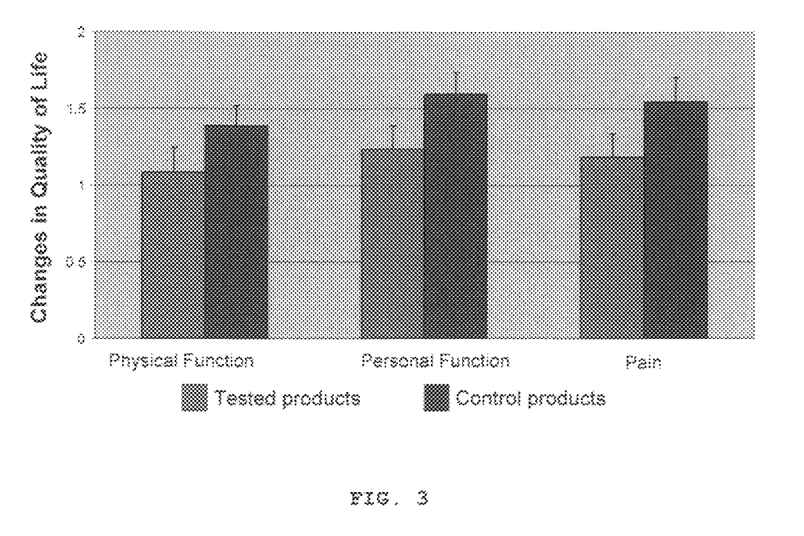
FIG. 3 represents the changes detected in quality of life related to xerostomia after the use of usual products for dry mouth (control products) and the composition of the invention (tested products).

FIG. 3 represents the changes detected in quality of life related to xerostomia after the use of usual products for dry mouth (control products) and the composition of the invention (tested products). The quality of life of the subjects is greater the smaller the value is. Significant differences were found between the groups: physical function (p=0.03), personal function (p=0.03) and pain (p=0.01).

A significant improvement was detected after the use of the tested products compared with the usual dry mouth treatment routine (control products): physical function (p=0.03), pain (p=0.03) and personal function (p=0.01).

Example 7

Protective Capacity of the Composition of the Invention Against Tooth Demineralisation Compared to that of Olive Oil.

The protective capacity of a mouthwash formulated with olive oil, trimethylglycine and xylitol on enamel and dentin subjected to extreme erosion conditions compared with that of olive oil was analysed. For the evaluation of the effects, a control was included consisting of distilled water.

Materials and Methods

Sample Preparation

Incisive teeth extracted from a cow's jaw were used which were immersed in a 0.5% thymol solution at room temperature. The teeth were sectioned at the cementum-enamel junction by means of a water-cooled diamond scalpel (Exakt, Norderstedt, Germany), and the crowns and roots were embedded in acrylic resin cylinders (Paladur, Heraeus Kulzer, Wehrheim, Germany). Radicular cementum was completely eliminated. Enamel and dentin surfaces were then polished so that the thickness of the outermost layer of enamel and dentin was reduced to approximately 200 µm, controlling this by means of a micrometer (Digimatic®, Micrometer, Mitutoyo, Tokyo, Japan).

Each enamel and dentin sample was covered with adhesive tape (Tesa, Beiersdorf, Hamburg, Germany) on both sides, leaving an exposed window of 3 mm width. The adhesive tape thus protected the original surfaces that served as a reference in the profilometric measurement. The samples were stored in water until the time of the experiment.

Study Design

The specimens of enamel and dentin were subjected to 10 cycles of pre-treatment, remineralisation, demineralisation and remineralisation. Pre-treatment consisted in immersing each specimen for 5 minutes in one of the following preparations: (A) distilled water; (B) mouthwash with olive oil, trimethylglycine and xylitol; and (C) olive oil.

After the pre-treatment, the samples were rinsed with water and transferred to artificial saliva (Klimek et al, 1982) for 30 minutes. Demineralisation was subsequently carried out by immersing the specimens in a 1% citric acid solution (pH: 2.3) for 3 minutes. After demineralisation, the samples were rinsed with water and once again transferred to the artificial saliva, this time for 60 minutes. This complete cycle (5 minutes of pre-treatment, 30 minutes in artificial saliva, 3 minutes in erosive conditions and 60 minutes in artificial saliva) was repeated 10 times.

Profilometric Measurements

Loss of enamel and dentin was quantified performing profile or profilometric measurements (Mahr Perthometer, Göttingen, Germany). Prior to the experiment, baseline measurements were taken that would serve to evaluate the surfaces that would be used as reference to calculate the losses in enamel and dentin after the experiments. To this end, six marks were performed in the centre of each specimen at 1000 µm intervals. The length of the profile measurements is performed along 250 µm with data collection every 0.69 µm. After the experiment the adhesive tapes were removed and the samples were analysed again. The average depth of the eroded surfaces was thus calculated with respect to basic surface profiles by means of specific software (Mahr Perthometer Concept 7.0, Mahr, Göttingen, Germany).

Statistical Analysis

The loss of enamel and dentin was calculated (mean±standard deviation) for each group and statistically analysed by Student's t test followed by Bonferroni's t test for multiple comparisons (Statistica 6.0, Statsoft, Tulsa, USA).

Results

Figure 4:
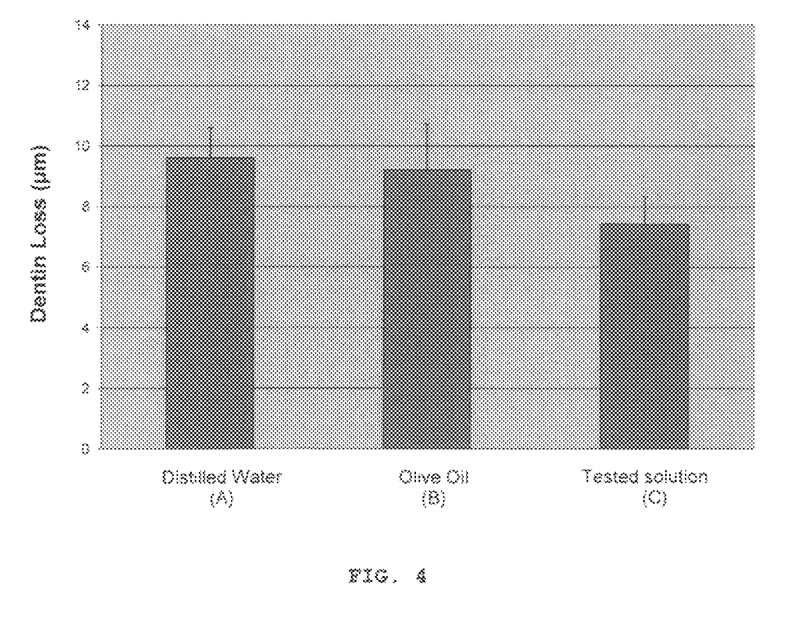
FIG. 4 represents dentin loss under conditions of extreme erosion using distilled water, olive oil and the composition of the invention (tested solution).

The mean value for dentin loss in the three groups is shown in FIG. 4.

Dentin loss in the control group (A) was 9.6 µm±1.0. The results obtained with olive oil (B) do not show differences with respect to distilled water (9.21 µm±1.5). The tested solution (C) shows an improvement with respect to water and olive oil (7.41 µm±0.9) although said improvement is significant only for water.

Figure 5:
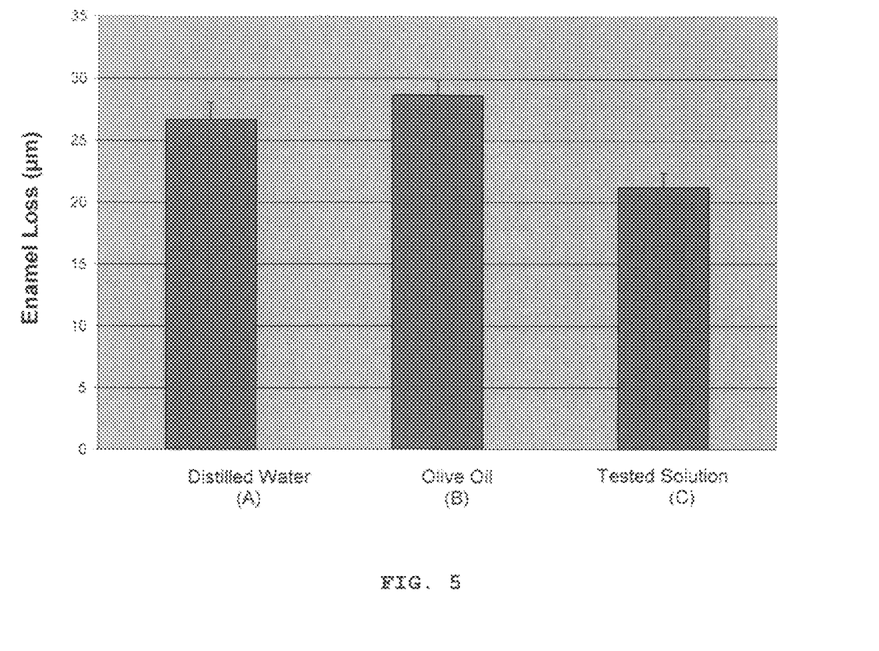
FIG. 5 represents enamel loss under conditions of extreme erosion using distilled water, olive oil and the composition of the invention (tested solution).

The mean value for enamel loss in the three groups is shown in FIG. 5.

Dentin loss in the control group (A) was 26.7 µm±1.3. The results obtained with olive oil (B) do not show differences with respect to distilled water (28.7 μm±1.8). The tested solution (C) shows a significant improvement with respect to water and olive oil (21.2 μm±1.1).

Therefore, although 100% olive oil does not exert any protection against the demineralising conditions of an acid solution at a pH of 2.3, the composition of the invention, however, has a marked protective effect on enamel and dentin against demineralising conditions.

Example 8

Protective Capacity of the Composition of the Invention Against Tooth Demineralisation Compared to that of the Three Ingredients Thereof Separately The protective capacity of a mouthwash formulated with olive oil, trimethylglycine and xylitol in dentin subjected to extreme erosion conditions was analysed, compared to that of aqueous solutions of the three ingredients separately in the same concentrations used in the mouthwash tested. For the evaluation of effects a control was included consisting of distilled water.

Materials and Methods

Sample Preparation

Incisive teeth extracted from a cow's jaw were used, which were immersed in a 0.5% thymol solution at room temperature. The teeth were sectioned at the cementum-enamel junction by means of a water-cooled diamond scalpel (Exakt, Norderstedt, Germany), and the crowns and roots were embedded in acrylic resin cylinders (Paladur, Heraeus Kulzer, Wehrheim, Germany). Radicular cementum was completely eliminated. Dentin surfaces were then polished so that the thickness of the outermost layer of dentin was reduced to approximately 200 μm, controlling this with a micrometer (Digimatic®, Micrometer, Mitutoyo, Tokyo, Japan).

Each dentin sample was covered with adhesive tape (Tesa, Beiersdorf, Hamburg, Germany) on both sides, leaving an exposed window of 3 mm width. The adhesive tape thus protected the original surfaces that would serve as a reference in the profilometric measurement. The samples were stored in water until the time of the experiment.

Study Design

The dentin specimens were subjected to 10 cycles of pre-treatment, remineralisation, demineralisation and remineralisation. Pre-treatment consisted in immersing each specimen for 5 minutes in one of the following preparations: (A) distilled water; (B) mouthwash with olive oil, trimethylglycine and xylitol; (C) 2% emulsion of olive oil in water; (D) 2% aqueous solution of trimethylglycine; and (E) 1% aqueous solution of xylitol. Solutions C, D and E are prepared with the same percentages in which the ingredients form part of tested mouthwash B. The 2% emulsion of olive oil in water was prepared by means of a high-speed mixer prior to each treatment, resulting in a finely dispersed emulsion.

After the pre-treatment, the samples were rinsed with water and transferred to artificial saliva (Klimek et al, 1982) for 30 minutes. Demineralisation was subsequently carried out by immersing the specimens in a 1% citric acid solution (pH: 2.3) for 3 minutes. After demineralisation, the samples were rinsed with water and once again transferred to the artificial saliva, this time for 60 minutes. This complete cycle (5 minutes of pre-treatment, 30 minutes in artificial saliva, 3 minutes in erosive conditions and 60 minutes in artificial saliva) was repeated 10 times.

Profilometric Measurements

Dentin loss was quantified performing profile or profilometric measurements (Mahr Perthometer, Göttingen, Germany). Prior to the experiment, baseline measurements were taken that would serve to evaluate the surfaces that would be used as reference to calculate the losses in dentin after the experiments. To this end, six marks were performed in the centre of each specimen at 1000 μm intervals. The length of the profile measurements is performed along 250 μm with data collection every 0.69 μm. After the experiment the adhesive tapes were removed and the samples were analysed again. The average depth of the eroded surfaces was thus calculated with respect to basic surface profiles by means of specific software (Mahr Perthometer Concept 7.0, Mahr, Göttingen, Germany).

Statistical Analysis

Dentin loss was calculated (mean±standard deviation) for each group and statistically analysed by Student's t test followed by Bonferroni's t test for multiple comparisons (Statistica 6.0, Statsoft, Tulsa, USA).

Results

Figure 6:
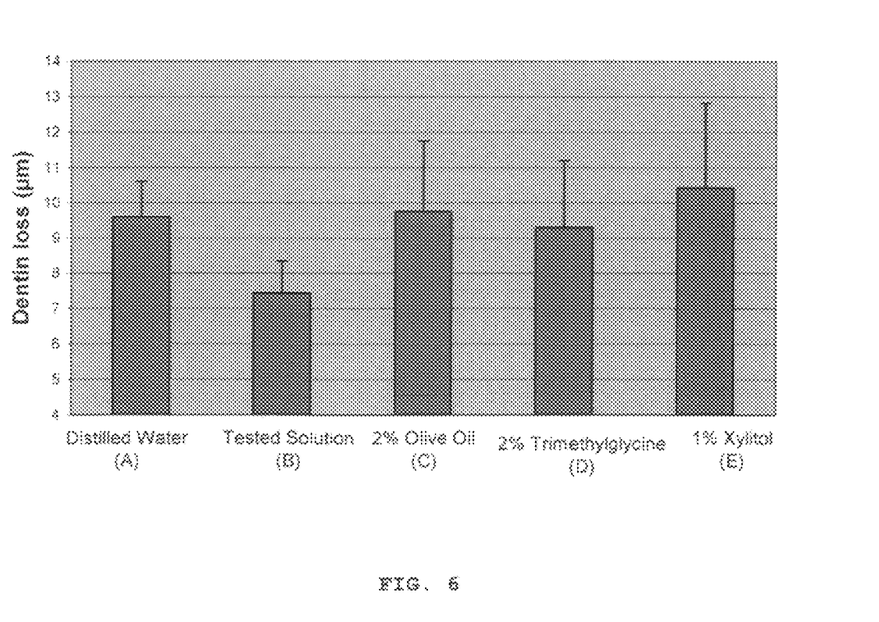
FIG. 6 represents dentin loss under conditions of extreme erosion using distilled water, the composition of the invention and solutions of each one of the three components thereof (2% olive oil, 2% trimethylglycine and 1% xylitol).

Mean dentin loss in groups A-E is shown in FIG. 6.

Dentin loss in the control group (A) was of 9.6 μm±1.0. The tested solution (B) was the only one that demonstrated a protective effect against erosion (7.4 μm±0.9), whereas application of the 2% olive oil emulsion (C), the 2% trimethylglycine solution (D) and the 1% xylitol solution (E) did not demonstrate any protective effect on dentin.

The invention claimed is:

1. A composition for treating xerostomia characterised in that it comprises 0.1-4% by weight of olive oil, 0.1-6% by weight of trimethylglycine and 1-50% by weight of xylitol.

2. A composition according to claim 1, characterised in that it comprises 0.2-3% by weight of olive oil.

3. A composition according to claim 2, characterised in that it comprises 2% by weight of olive oil.

4. A composition according to claim 1, characterised in that it comprises 4% by weight of trimethylglycine.

5. A composition according to claim 1, characterised in that it comprises 5-30% by weight of xylitol.

6. A composition according to claim 5, characterised in that it comprises 10% by weight of xylitol.

7. A composition according to claim 1, characterised in that it comprises 2% by weight of olive oil, 4% by weight of trimethylglycine and 10% by weight of xylitol.

8. A composition according to claim 1, characterised in that it comprises 2% by weight of olive oil, 2% by weight of trimethylglycine and 1% by weight of xylitol.

9. A composition according to claim 1, characterized in that it comprises one or more components selected from the group constituted by remineralising agents, viscosity-controlling agents, moisturising agents, preservatives, colorants, buffer agents, sweeteners, proteolytic enzymes, emulsifiers, abrasives, essential oils, cicatrizing agents, aromas, antioxidants, plant and animal gelatines, excipients, and a mixture thereof.

10. A composition according to claim 1, comprising 1% by weight of olive oil.

11. A composition according to claim 1, comprising 1% by weight of olive oil, 4% by weight of trimethylglycine, and 10% by weight of xylitol.

12. A composition according to claim 1, characterised in that it is formulated as a toothpaste, mouthwash, salivary substitute, spray, gel, chewing gum, suckable capsules, suckable lozenges, palate sheets, tablets, sweets, impregnated oral swabs, impregnated oral gauzes, suckable single-dose presentations of frozen solution.

* * * * *